United States Patent
Mercati et al.

(10) Patent No.: US 11,083,691 B2
(45) Date of Patent: Aug. 10, 2021

(54) COMPOSITIONS CONTAINING SYSTEMS OF RELEASE OF CARBON DIOXIDE OBTAINED FROM PLANT JUICES

(71) Applicant: Aboca S.p.A. Società Agricola, Sansepolcro (IT)

(72) Inventors: Valentino Mercati, Sansepolcro (IT); Luca Rampoldi, Sansepolcro (IT); Caroline Pelucchini, Sansepolcro (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 78 days.

(21) Appl. No.: 16/614,480

(22) PCT Filed: May 10, 2018

(86) PCT No.: PCT/IB2018/053255
§ 371 (c)(1),
(2) Date: Nov. 18, 2019

(87) PCT Pub. No.: WO2018/211372
PCT Pub. Date: Nov. 22, 2018

(65) Prior Publication Data
US 2020/0093741 A1 Mar. 26, 2020

(30) Foreign Application Priority Data
May 19, 2017 (IT) .................. 102017000054380

(51) Int. Cl.
| | | |
|---|---|---|
| *A61K 9/02* | (2006.01) | |
| *A61K 9/00* | (2006.01) | |
| *A61K 47/36* | (2006.01) | |
| *A61K 47/44* | (2017.01) | |
| *A61K 47/46* | (2006.01) | |
| *A61K 9/19* | (2006.01) | |

(52) U.S. Cl.
CPC .............. *A61K 9/02* (2013.01); *A61K 9/0031* (2013.01); *A61K 9/19* (2013.01); *A61K 47/36* (2013.01); *A61K 47/44* (2013.01); *A61K 47/46* (2013.01)

(58) Field of Classification Search
None
See application file for complete search history.

(56) References Cited

FOREIGN PATENT DOCUMENTS

| EP | 1043023 B1 | 10/2000 | |
|---|---|---|---|
| GB | 917456 A | * 2/1963 | ............. A61K 33/42 |
| WO | WO-2018211372 A1 | 11/2018 | |

OTHER PUBLICATIONS

Hakata, T., et al., "Effects of Bases and Additives on Release of Carbon Dioxide from Effervescent Suppositories," Chemical and Pharmaceutical Bulletin 41(2):351-356, Pharmaceutical Society of Japan, Japan (1993).

International Search Report and Written Opinion dated Sep. 18, 2018, for International Application No. PCT/IB2018/053255, European Patent Office, Netherlands, 34 pages.

* cited by examiner

*Primary Examiner* — Melissa S Mercier
(74) *Attorney, Agent, or Firm* — Sterne, Kessler, Goldstein & Fox P.L.L.C.

(57) ABSTRACT

The present application relates to compositions for the release of carbon dioxide following rectal administration comprising acid plant juices supported on gum and at least a salt of carbonic acid. Such compositions resulted to be particularly effective in stimulating evacuation, in particular showed an optimum kinetics of carbon dioxide release.

16 Claims, No Drawings

COMPOSITIONS CONTAINING SYSTEMS OF RELEASE OF CARBON DIOXIDE OBTAINED FROM PLANT JUICES

The present application relates to compositions for the release of carbon dioxide after rectal administration comprising acid plant juices supported on gum and at least a salt of carbonic acid. Such compositions resulted to be particularly effective in stimulating evacuation, in particular showed an optimum kinetics of carbon dioxide release.

STATE OF PRIOR ART

The evacuation disorders, in particular constipation, are a very widespread problem. A mechanism for causing evacuation is given by the release of carbon dioxide by suppositories.

For producing carbon dioxide, an organic acid and an alkaline salt of carbonic acid are commonly used which are capable of producing, in the neutralization reaction, the carbonic acid which, instable in acid and neutral environment, decomposes by producing carbon dioxide.

A scheme of such reaction is the following:

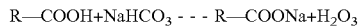

R—COOH+NaHCO$_3$ - - - R—COONa+H$_2$O$_3$

H$_2$CO$_3$ - - - H$_2$O+CO$_2$

R can be a saturated or unsaturated aliphatic chain or an aromatic system or a combination of both of them.

In the state of art, a product is described and commercialized which uses this mechanism. Such product is constituted by a hydrophilic mass formed by derivatives of polyethylene glycol (PEG) wherein alkaline Salts of organic acids and Salts of partially neutralized organic acids are dispersed so as to produce the carbon dioxide.

However, the evolution of natural treatment concept requires the formulation of preparations without synthesis components existing instead in the products known in the state of art.

Then, it is of interest developing compositions to ease evacuation by means of the release of carbon dioxide without synthesis components.

SUMMARY OF THE INVENTION

For preparing natural mixtures suitable to the release of carbon dioxide after rectal administration, as source of organic acids, plant juices can be used, in particular fruit juices and, as bases, salts of the acid or plant juices, in particular fruit juices, partially neutralized with alkaline substances and, as bases, Salts of the carbonic acid. Upon preparing these mixtures the inventors found a first technical problem, that is the fact of obtaining a fruit juice or a partially neutralized fruit juice at the solid state, since the sugars contained in the plant juices and in particular in the fruit juices show problems during drying. Sugars, as they are strongly hygroscopic, keep a water portion. This water, if existing in the suppository, is going to trigger immediately the effervescence reaction, actually by making the suppository unusable for the prefixed target. Moreover, during experimentations, apart from the above-mentioned technical problem, the inventors observed a second technical problem, that is the interference of the supports, in the time period for triggering the effervescence reaction when inserted in the suppositories. Under the term support, in the present description a technological adjuvant is meant which allows to obtain, starting from a liquid or pasty juice, a workable solid powder.

When supported fruit juices were used, apart from the problem of residual humidity, a decrease in amount and speed of the release of carbon dioxide by the suppository in fact was noted. Moreover, experiments on some healthy volunteers showed the reduced, and in several cases the total, loss of evacuating power of the suppositories prepared in this way, that is by using fruit juices supported with the most common supports used in these cases as better described hereinafter.

In experiments one tested even technological adjuvants used in the food field to help in solidifying natural extracts such as talcum, silicon dioxide, silicas, however they resulted to be of little use and in some cases the drying difficulty even increased. An acceptable improvement from the residual humidity point of view was obtained by using starches (rice, corn, potato, tapioca starch) and starch derivatives such as maltodextrins, however the release of carbon dioxide was not satisfying.

In the class of carbohydrates monosaccharides, disaccharides, trisaccharides were tested and, as expected, humidity, and above all the difficulty in releasing carbon dioxide, was growing as the number of monomeric units increased, that is going from monosaccharides to trisaccharides. Monosaccharides (fructose, glucose, mannitol, sorbitol), disaccharides (sucrose, maltose, lactose), trisaccharides (maltotriose, raffinose, stachyose) were further tested. By further increasing the number of monomeric units and the molecule complexity, a still greater reduction in the kinetics of carbon dioxide release was expected. The kinetics of carbon dioxide release is defined as the amount of gas which is emitted by the suppository in the time unit. This deduction is expected even by the fact that carbohydrates like gums, for example Arabic gum, xanthan gum, guar gum, tare gum, konjac gum, locust bean gum, upon contacting water are likely to form a gel. These gums, in fact, are conveniently exploited for delayed releases in drugs. Surprisingly, however, the inventors observed that the combination of gums with plant juices, in particular with fruit juices, produced instead a faster release kinetics than the one obtained with monosaccharides, disaccharides and trisaccharides. Moreover, the residual humidity of powders obtained both only with fruit juice and with partially neutralized fruit juice was very low and prevented the effervescence reaction from being triggered. By using this combination suppositories were obtained which were stable in time and suitable to the purpose. The effectiveness was confirmed even in a clinical trial wherein 16 subjects out of 17 evacuated correctly and in a time period lower than 15 minutes.

Therefore, the invention relates to:

A composition for the release of carbon dioxide following rectal administration comprising a mixture selected from:

a) acid plant juice supported on gum and a salt of carbonic acid;

b) plant juice partially neutralized with an alkaline substance supported on gum and a salt of carbonic acid;

c) acid plant juice and plant juice partially neutralized with an alkaline substance both supported on gum and a salt of carbonic acid.

A process for preparing the herein described compositions comprising the following steps:

i) preparing one or more of the following mixtures:

a) acid plant juice supported on gum and a salt of carbonic acid;

b) plant juice partially neutralized with an alkaline substance supported on gum and a salt of carbonic acid;

c) acid plant juice and plant juice partially neutralized with an alkaline substance both supported on gum and a salt of carbonic acid;

ii) adding to said mixtures one or more substances suitable for the preparation of rectal administration formulations.

DETAILED DESCRIPTION OF THE INVENTION

The present invention relates to compositions suitable to the release of carbon dioxide if administered by rectal route comprising a salt of carbonic acid and an acid plant juice supported on gum and/or a plant juice partially neutralized with an alkaline substance the neutralization product thereof is supported on gum too.

In the present description under the expression "Composition for the release of carbon dioxide following rectal administration" any composition is meant, in particular a composition in form of suppository, suitable to be administered by rectal route and to release $CO_2$ when administered in rectum.

In the present description under the expression "plant juice or fruit juice supported on gum" a physical mixture in the solid state is meant comprising a substance present in lower amount, that is the juice, dispersed in an agent existing in greater amount, that is the gum support.

In the present description under the expression "partially neutralized with an alkaline substance" an acid solution is meant that after adding an alkaline substance shows a pH lower than 7.

Examples of alkaline substances which can be used to neutralize the plant juice are sodium, potassium and magnesium salts of carbonic, citric, phosphoric, sulfuric, tartaric, malic acid or mixtures thereof.

Examples of Salts of carbonic acid are sodium carbonate, potassium carbonate, magnesium carbonate, calcium carbonate, sodium acid carbonate, magnesium acid carbonate, potassium acid carbonate, sodium acid carbonate.

As gums, natural gums could be used, for example Arabic gum, xanthan gum, konjac gum, tare gum, guar gum, ghatti gum or mixtures thereof.

In the mixtures plant juices, that is juices obtained from plant portions, could be used, such as for example aloe juice, and in particular fruit juices such as for example orange juice, lemon juice, pineapple juice, apple juice, blackberry juice, blueberry juice, grapefruit juice, pear juice or mixtures thereof.

A juice having a pH lower or equal to 6 is defined as plant juice or acid fruit juice.

The base components of the mixture could be used in the following proportions 10 portions of fruit juice 0.1-10 portions of support, under portions the weight units are meant and, if one wishes to obtain a partially neutralized fruit juice, an amount of alkaline substance allowing to obtain a solution at the end of the neutralization reaction with a pH higher than 6.

According to an embodiment the composition will include an acid plant juice supported on gum and/or a plant juice partially neutralized with an alkaline substance supported on gum dried by means of spray dryer or freeze-drying.

The present invention further relates to compositions for rectal administering including the above-described mixtures in form of suppository or ovule. The suppositories could be prepared with hydrophilic agents, in particular PEG and/or glycerin, moreover they could be prepared with a lipophilic portion consisting of mono and triglycerides of natural and/or synthetic fatty acids.

According to an embodiment the compositions could further comprise cocoa butter, honey and/or beeswax and they could be prepared as described in the patent application IT number 102014902243945.

For example, suppositories could be prepared by using the mixtures according to the invention with compositions consisting of 5 to 17 portions by weight of beeswax, 5 to 25 portions by weight of honey, and 65 to 90 portions by weight of cocoa butter for a total amount of 100 portions.

According to an embodiment the compositions could include an amount of mixture selected from a), b) or c) ranging between 5 and 40% by weight, preferably between 10 and 40% by weight. Wherein under percentage by weight the percentage of grams per 100 g of composition is meant.

Not limiting examples of compositions of the invention are shown hereinafter, apt to be implemented in form of suppository:

| Substance | Comp. 1 | Comp. 2 | Comp. 3 | Comp. 4 |
|---|---|---|---|---|
| Mixture on gum support | 5 | 30 | 20 | 40 |
| Cocoa butter | 75 | 59 | 65 | 35 |
| Beeswax | 10 | 5 | 1 | 3 |
| Honey | 5 | 1 | 9 | 2 |

The amounts shown in the table are expressed in percentage by weight with respect to 100 g of composition.

The composition according to the present description could be implemented in form of medical device according to any one of the classes described in the EC Directory 93/42 on the medical devices (which comprises even substances and not only "devices" in the mechanical meaning of the term) or in any suitable form according to the regulatory provisions of the country wherein such composition will be produced.

The compositions of the invention can be used for their properties of stimulating evacuation by producing $CO_2$. Therefore, the invention further relates to the composition of the invention as herein described and claimed for use in the treatment of constipation.

The invention further relates to a therapeutic treatment wherein a formulation, mixture or composition according to the invention is administered to a patient requiring it.

The invention further relates to a process for preparing the compositions as defined in the present description and in the claims comprising the following steps:

i) preparing a mixture of acid plant juices supported on gum and at least a salt of carbonic acid;

ii) adding to said mixture one or more substances suitable for the preparation of rectal administration formulations.

The mixtures for producing CO2 could be prepared for example with one of these three combinations:

a. plant juice or acid fruit juice with alkaline substance and salt of carbonic acid;

b. plant juice or acid fruit juice and plant juice or fruit juice partially neutralized with an alkaline substance and salt of carbonic acid;

c. plant juice or fruit juice partially neutralized with alkaline substance and salt of carbonic acid.

By way of example the production of a partially neutralized fruit juice is illustrated:

a. 500 grams of sodium bicarbonate are added to 10 kg of lemon juice. The mixture is left to react until reaching a pH of 4.5;

b. 1.5 kg of Arabic gum are added to the solution obtained at the previous step until complete dissolution;

c. the solution obtained at the previous step is brought to the solid state by freeze-drying or spray dryer.

The mixtures could be prepared according to the following process:

1. an alkaline substance is added to the plant juice or acid fruit juice until reaching the wished pH. The solution is left to react for the time required to the reaction completion and until reaching the wished pH;

2. a support is added to the solution obtained at the step 1 and one stirs until complete solubilization;

3. the solution obtained at step 2 is brought to the dry status by spray dryer or freeze-drying. The passage 1 will be optional, if one wishes to obtain a plant juice or fruit juice not partially neutralized with an alkaline substance, in this case the neutralization phase will be omitted, directly adding the support.

According to an embodiment the process for preparing the composition comprises the following steps:

a. melting lipids and/or other components soluble or dispersible in the melt lipids b. adding to the molten mass obtained in step a) the mixture according to any one of the herein described combinations and one or more substances suitable for the preparation of rectal administration formulations;

c. pouring into suitable moulds and cooling down the obtained product until complete solidification.

According to an embodiment the process for preparing the composition comprises the following steps:

a. melting beeswax and cocoa butter at a temperature ranging from 70 and 85° C.;

b. adding to the molten mass obtained in step a) honey and the acid fruit juice, in particular the partially neutralized lemon juice and the sodium bicarbonate;

c. pouring into suitable moulds or containers.

Examples for preparing the mixtures and compositions of the invention are provided hereinafter and examples of formulations are provided only by way of demonstrating the possible embodiments of the invention and not for limiting purposes.

EXAMPLES

1. Example of Preparation of the Invention Mixture 100 kg of lemon juice were placed in a dissolver and kept under stirring at room environment. 15 kg of sodium bicarbonate were added to the lemon juice and the whole was kept under stirring until reaching a pH of 4.5.

After the reaction took place, 15 kg of Arabic gum were added and the whole was kept under stirring until complete dissolution of gum. After the dissolution took place, the mixture was brought to the dry state by spray drying (nebulization in atomizer).

Other mixtures of partially neutralized juices can be implemented with the above-described method as shown hereinafter.

The values shown in table are expressed in Kg

| Composition | 1 | 2 | 3 | 4 | 5 | 6 | 7 | 9 | 10 |
|---|---|---|---|---|---|---|---|---|---|
| lemon juice | 100 | | | | | 50 | 30 | | 10 |
| pineapple juice | | 100 | | | | 50 | | 10 | 10 |
| orange juice | | | 100 | | | | 10 | 40 | 10 |
| blackberry juice | | | | 100 | | | | 40 | 30 |
| elder juice | | | | | 100 | | 60 | 10 | 40 |
| Arabic gum | 15 | 5 | 30 | 100 | 20 | | 10 | | |
| Xanthan gum | | | | | 1 | | 2 | | 1 |
| guar gum | | | | | | 1 | | 3 | 1 |
| sodium bicarbonate | 15 | 50 | 3 | | | | 5 | | |
| tribasic sodium citrate | | | | 10 | | | 40 | | |
| potassium bicarbonate | | | | | | | | | |
| tribasic potassium carbonate | | | | | | | | | |
| tartrate | | | | | 10 | 40 | | | |
| magnesium carbonate | | | | | | | | | |
| potassium carbonate | | | | | | | | 10 | 5 |

2. Example of Preparation of the Invention Composition in Form of Suppository The mixture prepared according to example 1 was used to prepare the composition in form of suppository according to the following procedure:

a. melting beeswax and cocoa butter at a temperature comprised between 70-80° C.

b. after melting took place, cooling at a temperature comprised between 35-38° C.

c. adding, in the order, honey, partially neutralized lemon juice and sodium bicarbonate d. homogenizing the mixture obtained at the previous step and cooling at 26° C.

e. heating at 33° C. and distributing in the moulds.

3. Examples of Formulations in Form of Suppositories

The amounts are expressed in terms of % by weight

| Substance | Form. 1 | Form. 2 | Form. 3 | Form. 4 |
|---|---|---|---|---|
| beeswax | 1 | 2 | 3 | 1 |
| cocoa butter | 59 | 59 | 50 | 54 |
| partially neutralized lemon juice | 0 | 30 | 0 | 10 |
| partially neutralized orange juice | 23 | 0 | 32 | 10 |
| supported pineapple juice | 0 | 0 | 0 | 12 |
| Sodium bicarbonate | 3 | 0 | 5 | 0 |
| sodium carbonate | 0 | 5 | 0 | 4 |
| honey | 14 | 4 | 10 | 10 |

The above shown examples are purely indicative, it is clear that starting from the above examples and following the teachings of the present invention the person skilled in the art will be able to implement other formulations and compositions within the scope of the present invention.

The invention claimed is:

1. A composition for the release of carbon dioxide following rectal administration comprising a mixture selected from:
   a) acid plant juice supported on gum and a salt of carbonic acid;
   b) plant juice, partially neutralized with an alkaline substance, supported on gum and a salt of carbonic acid;
   c) acid plant juice and plant juice partially neutralized with an alkaline substance supported on gum and a salt of carbonic acid; wherein the composition is in the form of suppository or ovule.

2. The composition according to claim 1, wherein said alkaline substance is selected from the group consisting of sodium, potassium and magnesium salts of carbonic, citric, phosphoric, sulfuric, tartaric, and malic acid or mixtures thereof.

3. The composition according to claim 1, wherein said carbonic acid salt is selected from the group consisting of sodium acid carbonate, potassium acid carbonate, sodium carbonate, potassium carbonate, calcium carbonate, and magnesium carbonate.

4. The composition according to claim 1, wherein said plant juice is supported on a natural gum selected from the group consisting of Arabic gum, xanthan gum, konjac gum, tare gum, guar gum, ghatti gum or mixtures thereof.

5. The composition according to claim 1, wherein said plant juice is a fruit juice.

6. The composition according to claim 5, wherein said fruit juice is selected from the group consisting of orange juice, lemon juice, pineapple juice, apple juice, blackberry juice, blueberry juice, grapefruit juice, and pear juice or mixtures thereof.

7. The composition according to claim 1, wherein said plant juice supported on gum or said mixture is dried by spray-drying or freeze-drying.

8. The composition according to claim 1, further comprising cocoa butter, honey and/or beeswax.

9. The composition according to claim 1, comprising hydrophilic agents.

10. The composition according to claim 1, comprising a lipophilic portion consisting of mono-, di- and triglycerides of natural and/or synthetic fatty acids.

11. The composition according to claim 1, wherein said mixture is in an amount from 5 to 50% by weight.

12. A method of treating constipation in a subject comprising administering a therapeutically effective amount of the composition of claim 1.

13. The process for preparing a composition according to claim 1, comprising the following steps:
   i) preparing one or more of the following mixtures:
      a) acid plant juice supported on gum and a salt of carbonic acid;
      b) plant juice partially neutralized with an alkaline substance supported on gum and a salt of carbonic acid;
      c) acid plant juice and plant juice partially neutralized with an alkaline substance both supported on gum and a salt of carbonic acid;
   ii) adding to said mixtures one or more substances suitable for the preparation of rectal administration formulations.

14. The process according to claim 13 wherein said step i) for preparing the mixture comprises the following steps:
   (i) preparing a solution comprising said acid plant juice and/or said partially neutralized plant juice and said gum support;
   (ii) drying by spray drying or freeze-drying the solution obtained in step (i).

15. The process according to claim 13 comprising the following further steps:
   (i) melting lipids and/or other components soluble or dispersible in the melt lipids
   (ii) adding to the molten mass obtained in step said mixture and one or more substances suitable for the preparation of rectal administration formulations;
   c. pouring into suitable molds or containers the product obtained in step (ii) and cooling down until complete solidification.

16. The composition according to claim 9, wherein the hydrophilic agent is polyethylene glycol (PEG) and/or glycerin.

* * * * *